US 6,660,721 B2

(12) United States Patent
Devos et al.

(10) Patent No.: US 6,660,721 B2
(45) Date of Patent: Dec. 9, 2003

(54) ANTI-HCV NUCLEOSIDE DERIVATIVES

(75) Inventors: Rene Robert Devos, Welwyn Garden (GB); Christopher John Hobbs, Hertford (GB); Wen-Rong Jiang, Welwyn Garden (GB); Joseph Armstrong Martin, Harpenden (GB); John Herbert Merrett, Baldock (GB); Isabel Najera, St. Albans (GB)

(73) Assignee: Hoffmann-la Roche Inc., Nutley, NJ (US)

( * ) Notice: Subject to any disclaimer, the term of this patent is extended or adjusted under 35 U.S.C. 154(b) by 0 days.

(21) Appl. No.: 10/106,970

(22) Filed: Mar. 26, 2002

(65) Prior Publication Data

US 2003/0083307 A1 May 1, 2003

(30) Foreign Application Priority Data

May 23, 2001 (GB) ............................................. 0112617

(51) Int. Cl.$^7$ ......................... A01N 43/04; A61K 31/70
(52) U.S. Cl. ............................. 514/45; 514/42; 514/43; 514/46; 514/47; 514/48; 514/49; 514/52; 536/18.7; 536/22.1; 536/28.1; 536/28.6; 536/28.7
(58) Field of Search ............................. 514/23, 42, 43, 514/45, 46, 49, 47, 48, 52; 536/18.7, 22.1, 28.1, 28.6, 28.7

(56) References Cited

U.S. PATENT DOCUMENTS

| 5,587,362 A | 12/1996 | Chu et al. |
| 5,968,826 A | 10/1999 | Bennett et al. |
| 6,348,587 B1 * | 2/2002 | Schinazi et al. ............ 536/25.3 |

FOREIGN PATENT DOCUMENTS

| WO | WO 99/43691 | 9/1999 |
| WO | WO 02 32920 | 4/2002 |

OTHER PUBLICATIONS

Gish et al., Sem. Liver. Dis., vol. 19, pp. 35–47 (1999).
Lohmann et al., Science, vol. 285, pp. 110–113 (1999).
Wagner et al., Med. Res. Rev., vol. 20(6), pp. 417–451 (2000).
Bischofberger et al., Antiviral Research, vol. 27, pp. 1–17 (1995).
Krieger et al., J. Virol., vol. 75, pp. 4614–4624 (2001).
Ryan & Drew, EMBO., vol. 13, pp. 928–933 (1994).
Bartenschlager, J. Virol. vol. 71(11), pp. 8416–8428 (1997).
Thomas et al., Nucleotides and Nucleosides, vol. 13, pp. 309–323 (1994).
Tianwei M. et al., J. Med. Chem., vol. 39(14), pp. 2835–2843 (1996).
Tianwei M. et al, J. Med. Chem., vol. 40 (17), pp. 2750–2754 (1997).

* cited by examiner

*Primary Examiner*—James O. Wilson
*Assistant Examiner*—Patrick Lewis
(74) *Attorney, Agent, or Firm*—George W. Johnston; Dennis P. Tramaloni; Lyman H. Smith

(57) ABSTRACT

The present invention comprises nucleoside derivatives for use in the treatment or prophylaxis of hepatitis C virus infections. In particular, the present invention discloses the novel use of known 2'-deoxy-2'-fluoro nucleoside derivatives as inhibitors of hepatitis C virus (HCV) RNA replication and pharmaceutical compositions of such compounds. The compounds of this invention have potential use as therapeutic agents for the treatment of HCV infections.

3 Claims, No Drawings

ANTI-HCV NUCLEOSIDE DERIVATIVES

BACKGROUND OF THE INVENTION

Hepatitis C virus is the leading cause of chronic liver disease throughout the world. Patients infected with HCV are at risk of developing cirrhosis of the liver and subsequent hepatocellular carcinoma and hence HCV is the major indication for liver transplantation. Only two approved therapies are currently available for the treatment of HCV infection (R. G. Gish, Sem. Liver. Dis., 1999, 19, 35). These are interferon-α monotherapy and, more recently, combination therapy of the nucleoside analogue, ribavirin (Virazole), with interferon-α.

Hepatitis C virus belongs to the family of Flaviviridae. It is an RNA virus, the RNA genome encoding a large polyprotein which after processing produces the necessary replication machinery to ensure synthesis of progeny RNA. It is believed that most of the non-structural proteins encoded by the HCV RNA genome are involved in RNA replication. Lohmann et al. [V. Lohmann et al., Science, 1999, 285, 110–113] have described the construction of a human hepatoma (Huh7) cell line in which subgenomic HCV RNA molecules have been introduced and shown to replicate with high efficiency. It is believed that the mechanism of RNA replication in these cell lines is identical to the replication of the full length HCV RNA genome in infected hepatocytes. The subgenomic HCV cDNA clones used for the isolation of these cell lines have formed the basis for the development of a cell-based assay for identifying nucleoside analogue inhibitors of HCV replication.

2'-Fluoronucleoside analogues are described in WO 99/43691 as being useful in the treatment of hepatitis B infection, hepatitis C infection, HIV and abnormal cellular proliferation, including tumours and cancer. 2'-Deoxy-2'-fluoro ribonucleoside derivatives are not described specifically.

SUMMARY OF THE INVENTION

The present invention comprises the novel use of known 2'-deoxy-2'-fluoro nucleoside derivatives as inhibitors of hepatitis C virus (HCV) RNA replication and pharmaceutical compositions of such compounds. The compounds of this invention are therefore of use as therapeutic agents for the treatment of HCV infections.

DETAILED DESCRIPTION OF THE INVENTION

The present invention describes the use of 2'-deoxy-2'-fluoro nucleoside derivatives of formula I

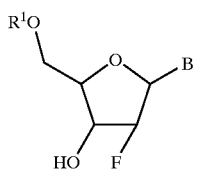

I wherein
$R^1$ is hydrogen or phosphate and
B signifies a 1-pyrimidinyl or 9-purinyl residue of formulae B1, B2 or B3

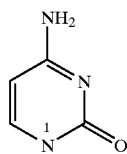

B1

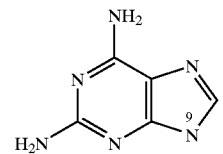

B2

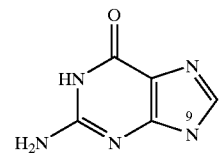

B3 and of pharmaceutically acceptable salts thereof for the treatment of diseases mediated by the hepatitis C virus (HCV) or for the preparation of medicaments for such treatment.

The term "phosphate" as used herein for $R^1$, denotes a monophosphate, diphosphate or triphosphate group of the formula —[P(=O)(OH)O]$_n$H, wherein n is an integer selected from 1, 2 and 3. Phosphate in $R^1$ is preferably a monophosphate group. The term "phosphate" further includes stabilized monophosphate prodrugs or other pharmaceutically acceptable leaving groups which, when administered in vivo, are capable of providing a compound wherein $R^1$ is monophosphate. These "pronucleotides" can improve the properties such as activity, bioavailability or stability of the parent nucleotide.

Examples of substituent groups which can replace one or more of the hydrogens in the monophosphate moiety are described in C. R. Wagner et al Medicinal Research Reviews, 2000, 20(6), 417 or in R. Jones and N. Bischofberger, Antiviral Research 1995, 27, 1. Such pronucleotides include alkyl and aryl phosphodiesters, steroid phosphodiesters, alkyl and aryl phosphotriesters, cyclic alkyl phosphotriesters, cyclosaligenyl (CycloSal) phosphotriesters, S-acyl-2-thioethyl (SATE) derivatives, dithioethyl (DTE) derivatives, pivaloyloxymethyl phosphoesters, para-acyloxybenzyl (PAOB) phosphoesters, glycerolipid phosphodiesters, glycosyl lipid phosphotriesters, dinucleosidyl phosphodiesters, dinucleoside phosphotriesters, phosphorodiamidatescyclic phosphoramidates, phosphoramidate monoesters and phosphoramidate diesters.

The invention also includes pro-drugs or bioprecursors of the parent nucleoside which are converted in vivo to the compound of formula I wherein $R^1$ is hydrogen or physiologically acceptable salts thereof. Preferred pro-drug derivatives include carboxylic ester derivatives of the 3'- or 5'-hydroxyl group in which the non-carbonyl moiety of the ester group is selected from straight or branched alkyl (e.g. methyl, n-propyl, n-butyl or tert.-butyl), alkoxyalkyl (e.g. methoxymethyl), araalkyl (e.g. benzyl), aryloxyalkyl (e.g. phenoxymethyl), aryl (e.g. phenyl optionally substituted by halogen, $C_{1-4}$ alkyl or $C_{1-4}$ alkoxy or amino); sulphonate esters such as alkylsulphonyl or arylsulphonyl (e.g. methanesulphonyl); amino acid esters (e.g. L-valyl or L-isoleucyl) or pharmaceutically acceptable salts thereof. The preparation is carried out according to known methods in the art, for example methods known from textbooks on organic chemistry e.g. from J. March (1992), "Advanced Organic Chemistry: Reactions, Mechanisms, and Structure", 4$^{th}$ ed. John Wiley & Sons).

In the pictorial representation of the compounds given throughout this application, a thickened tapered line (▬◣) indicates a substituent which is above the plane of the ring and a dotted line (·ııııı) indicates a substituent which is below the plane of the ring.

Compounds of the present invention exhibit stereoisomerism and therefore include compounds wherein the carbon atoms have the S, R, or R,S-configuration. The compounds of this invention can be any isomer of the compound of formula I or mixtures of these isomers. The compounds and intermediates of the present invention having one or more asymmetric carbon atoms may be obtained as mixtures of stereoisomers which can be resolved, at the appropriate steps in the process of this invention by stereospecific methods known in the art to obtain a given stereoisomer or pure enantiomer having a desired stereoconfiguration. Alternatively, the desired isomers may be directly synthesised by methods known in the art.

In a preferred embodiment of the invention the ribofuranoside is a α-D, β-D, α-L or β-L ribofuranosyl ring, more preferred a β-D or β-L ribofuranosyl ring, and most preferred a β-D ribofuranosyl ring.

The preferable relative configuration of compounds of this invention is that of formula I-a,

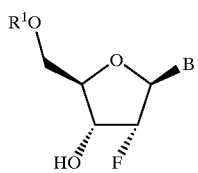

I-a wherein
R$^1$ and B are as defined above, and of pharmaceutically acceptable salts thereof.

Compounds of formula I exhibit tautomerism (as known from textbooks on organic chemistry e.g. J. March (1992), "Advanced Organic Chemistry: Reactions, Mechanisms, and Structure", 4$^{th}$ ed. John Wiley & Sons) that means that the compounds of this invention can exist as two or more chemical compounds that are capable of facile interconversion. In many cases it merely means the exchange of a hydrogen atom between two other atoms, to either of which it forms a covalent bond. Tautomeric compounds exist in a mobile equilibrium with each other, so that attempts to prepare the separate substances usually result in the formation of a mixture that shows all the chemical and physical properties to be expected on the basis of the structures of the components.

The most common type of tautomerism is that involving carbonyl, or keto, compounds and unsaturated hydroxyl compounds, or enols. The structural change is the shift of a hydrogen atom between atoms of carbon and oxygen, with the rearrangement of bonds.

For example, in many aliphatic aldehydes and ketones, such as acetaldehyde, the keto form is the predominant one; in phenols, the enol form is the major component. An intermediate situation is represented for example in ethyl acetoacetate, which at room temperature contains about 92.4% keto and 7.6% enol; at −78° C., the interconversion of the two forms is slow enough for the individual substances to be isolated.

It will be appreciated that within the present invention compounds of formula I exist in various tautomeric forms and that they are encompassed by the present invention.

Preferred tautomeric forms are drawn below:

2'-Deoxy-2'-fluorocytidine:

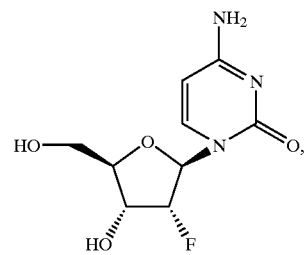

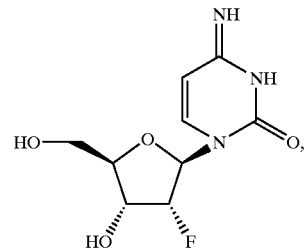

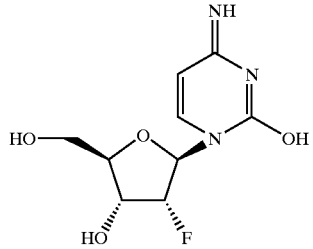

2-amino-2'-deoxy-2'-fluoroadenosine:

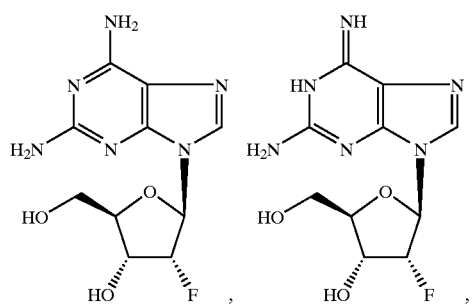

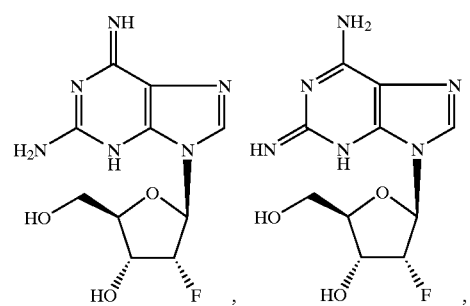

2'-deoxy-2'-fluoroguanosine:

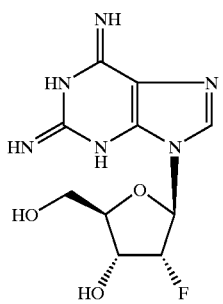

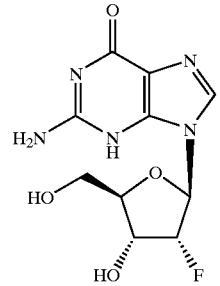

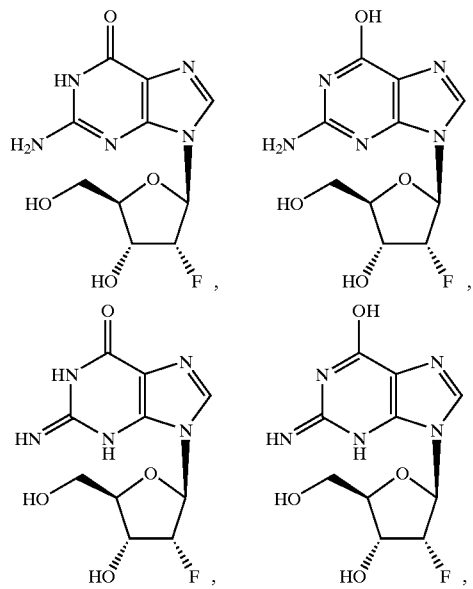

The above compounds preferably exist in the form drawn first.

Compounds of formula I which are basic can form pharmaceutically acceptable salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluene sulphonic acid, and the like). The formation and isolation of such salts can be carried out according to methods known in the art.

Compounds of formula I which are acidic can form pharmaceutically acceptable base salts derived from appropriate bases such as alkali metals (e.g. lithium, sodium, potassium), alkaline earth metals (e.g. calcium, magnesium), ammonium or $NX_4^+$ (wherein X is $C_{1-4}$ alkyl, preferably methyl or ethyl, more preferred methyl).

A preferred embodiment of the invention is the use of compounds of formula I or I-a as defined above wherein $R^1$ is as defined above and B signifies 1-pyrimidinyl, and of pharmaceutically acceptable salts thereof.

More preferred embodiments of compounds of formula I for the use in the treatment of diseases mediated by the hepatitis C virus (HCV) or for the preparation of a medicament for such treatment are set out in table 1 (see below):

TABLE 1

| Example | Structure | Name |
|---|---|---|
| 1 | 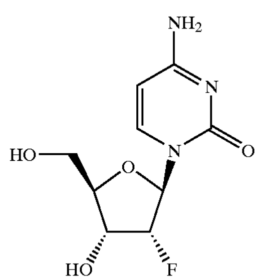 | 2'-Deoxy-2'-fluorocytidine |
| 2 | 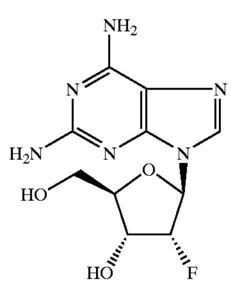 | 9-(2-Deoxy-2-fluoro-β-D-ribofuranosyl)-2,6-diaminopurine |

TABLE 1-continued

| Example | Structure | Name |
|---|---|---|
| 3 | 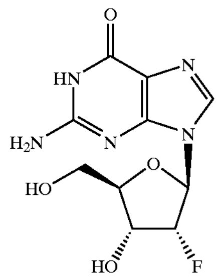 | 2'-Deoxy-2'-fluoroguanosine |
| 4 | 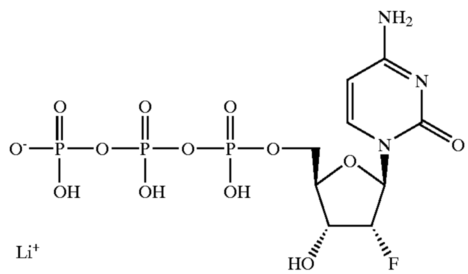 | 2'-Deoxy-2'-fluorocytidine 5'-O-triphosphate mono lithium salt |

Assay Methods

The activity of 2'-deoxy-2'-fluorocytidine was determined using an adaptation of the method reported by Lohmann et al [V. Lohmann et al., Science, 1999, 285, 110–113].

HCV Replicon Assay:

The HCV replicon-containing cell line was used to demonstrate the ability of 2'-deoxy-2'-fluorocytidine to inhibit the replication of HCV replicon RNA in cells. Since the replicon RNA replication mimics the replication of the HCV RNA in infected hepatocytes, it is believed that those small molecules that have the above property are interesting for further development as anti-HCV drugs.

The inhibition of the HCV replicon RNA replication will lead to a decrease of the replicon RNA in the cell, which can be measured using a method that specifically quantifies this RNA.

The assay is based on the idea of using a reporter as a simple readout for intracellular HCV replicon RNA level. For this purpose the Renilla luciferase gene was introduced into the first open reading frame of a replicon construct NK5.1 (Krieger et al., J. Virol. 75:4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928–933). After in vitro transcription the RNA was electroporated into human hepatoma Huh7 cells, and G418-resistant colonies were isolated and expanded. Stably selected cell line 2209-23 was shown to contain replicative HCV subgenomic RNA, and the activity of Renilla luciferase expressed by the replicon reflects its RNA level in the cells.

For the assay procedure, Renilla Luciferase HCV replicon cells (2209-23) that cultured in Dulbecco's MEM (GibcoBRL cat no. 31966-021) with 5% fetal calf serum (FCS) (GibcoBRL cat no. 10106-169) were plated onto a 96-well plate at 5000 cells per well, and incubated overnight. Twenty-four hours later, different dilutions of chemical compounds in the growth medium were added to the cells, which were then further incubated at 37° C. for three days. The assay was carried out in duplicate plates, one in opaque white and one in transparent, in order to measure the activity and cytotoxicity of a chemical compound in parallel ensuring the activity seen is not due to reduction on cell proliferation.

At the end of the incubation time, the cells in the white plate were harvested and luciferase activity was measured by using a Dual-Luciferase reporter assay system (Promega cat no. E1960). All the reagents described in the following paragraph were included in the manufacturer's kit, and the manufacturer's instructions were followed for preparations of the reagents. Briefly, the cells were washed twice with 200 $\mu$l PBS (phosphate buffered saline; pH 7.0) per well and lysed with 25 $\mu$l of 1× passive lysis buffer prior to incubation at room temperature for 20 min. One hundred microliter of LAR II reagent was added to each well. The plate was then inserted into the LB 96V microplate luminometer (MicroLumatPlus, Berthold), and 100 $\mu$l of Stop & Glo reagent was injected into each well by the machine and the signal measured using a 2-second delay, 10-second measurement program. The $IC_{50}$, the concentration of the drug required for reducing the replicon level by 50% in relation to the untreated cell control value, can be calculated from the plot of the percentage reduction of the luciferase activity vs. drug concentration.

For the cytotoxicity assay, WST-1 reagent from Roche Diagnostic (cat no. 1644807) was used. Ten microliter of WST-1 reagent was added to each well including wells that contained media alone as blanks. Cells were then incubated for 1 to 1.5 hours at 37° C., and the OD value was measured by a 96-well plate reader at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration.

HCV NS5B Polymerase Assay (Hepatitis C Virus Non-Structural Protein 5B RNA-Dependent RNA Polymerase Assay):

In order to establish the mechanism of action of 2'-deoxy-2'-fluorocytidine the activity of the 5'-O-triphosphates was measured against HCV NS5B RNA-dependent RNA polymerase enzyme. For this procedure full length NS5B polymerase bearing a C-terminal 6-histidine tag was used (V Lohmann, U Herian and R Bartenschlager J Virol, 1997, 71(11), 8416).

Reaction mixtures containing final concentrations of 40 mM N-2-hydroxyethylpiperazine-N'-2-ethanesulphonic acid (HEPES) at pH 8.0, 4 mM dithiothreitol (DTT), 4 mM magnesium acetate, Poly(rI):Oligo(dC)$_{16}$ template (0.1 mg:0.01 mg; annealed by heating a mixture of 5 ml of 0.1 mg/ml Poly(rI) and 5 ml of 10 mg/ml Oligo(dC)$_{16}$ to 95° C. for 5 minutes and then cooling to 30° C. over 20 minutes) and 500 nM [3H]-cytidine 5'-triphosphate ([$^3$H]-CTP; specific activity 740 GBq/mmol) (Amerham Pharmacia Biotech) in 35 µl volume were incubated with 5 µl aqueous solutions of nucleoside triphosphate and left for 5 minutes at room temperature. Usually ten compound dilutions were used for each IC$_{50}$ determination. 10 µl of a 5 µg/ml solution of HCV NS5B polymerase was added and the mixture incubated for 2 hours at 30° C. Positive controls containing no compound and negative controls containing no enzyme were included in each assay.

Reactions were terminated by addition of 50 µl of 20% (v/v) trichloroacetic acid followed by incubation at 4° C. for 30 minutes. After filtering, washing 3 times with 200 µl portions of 10% (v/v) trichloroacetic acid and 3 times with 200 µl portions of 70% (v/v) ethanol then drying, the reaction product was quantified by adding 25 µl of scintillation cocktail (Ecoscint A purchased from National Diagnostics) followed by scintillation counting.

The concentration of compound (IC$_{50}$) required to reduce [$^3$H]-CTP incorporation by 50% relative to the control containing no compound was calculated from a plot of the radioactive response vs. nucleoside triphosphate concentration.

In the HCV Replicon assay, compounds of the formulas I range in activity from an IC$_{50}$ of about 0.01 to about 100 µM, with preferred compounds having a range of activity from about 0.01 to about 50 µM, more preferably about 0.01 to 30 µM, and most preferably about 0.01 to 15 µM.

| Stucture | Name | IC$_{50}$ (µM) |
|---|---|---|
| HCV Replicon assay: | | |
| [structure of 2'-Deoxy-2'-fluorocytidine] | 2'-Deoxy-2'-fluorocytidine | 0.74 |
| [structure of 9-(2-Deoxy-2-fluoro-β-D-ribofuranosyl)-2,6-diaminopurine] | 9-(2-Deoxy-2-fluoro-β-D-ribofuranosyl)-2,6-diaminopurine | 10 |
| [structure of 2'-Deoxy-2'-fluoroguanosine] | 2'-Deoxy-2'-fluoroguanosine | 62% @ 20 |

-continued

| Stucture | Name | IC$_{50}$ ($\mu$M) |
|---|---|---|
| HCV NS5B RdR polymerase assay: | | |
| [structure of 2'-deoxy-2'-fluorocytidine 5'-O-triphosphate mono lithium salt] | 2'-deoxy-2'-fluorocytidine 5'-O-triphosphate mono lithium salt | 1.8 |

The above data demonstrate, that 2'-deoxy-2'-fluoro nucleoside derivatives of formula I are inhibiting subgenomic hepatitis C virus replication in a hepatoma cell line. The mode of action has been confirmed by in vitro inhibition experiments with purified HCV NS5B polymerase and the 5'-O-triphosphate derivative of 2'-deoxy-2'-fluorocytidine. The compounds of formula I therefore have the potential to be efficacious as antiviral drugs for the treatment of HCV infections in humans, or are metabolized to compounds that exhibit such activity.

In another embodiment of the invention, the active compound or its derivative or salt can be administered in combination or alternation with another antiviral agent, such as an anti-hepatitis agent, including those of formula I. When the active compound or its derivative or salt is administered in combination or alternation with another antiviral agent its activity may be increased.

In certain pharmaceutical dosage forms, the pro-drug form of the compounds, including acylated (especially acetylated) derivatives, pyridine esters and various salt forms of the present compounds are preferred. One of ordinary skill in the art will recognise how to readily modify the present compounds to pro-drug forms to facilitate delivery of active compounds to a target site within the host organism or patient. One of ordinary skill in the art will also take advantage of favourable pharmacokinetic parameters of the pro-drug forms, where applicable, in delivering the present compounds to targeted site within the host organism or patient to maximise the intended effect of the compound.

The active compound can be administered as any derivative that upon administration to the recipient, is capable of providing directly or indirectly, the parent compound. Furthermore, the modifications can affect the biological activity of the compound, in some cases increasing the activity over the parent compound. This can easily be assessed by preparing the derivative and testing its anti-HCV activity according to the methods described herein.

The 2'-deoxy-2'-fluoro nucleoside derivatives provided by the present invention or the medicaments thereof may be used in monotherapy or combination therapy, i.e. the treatment may be in conjunction with the administration of one or more additional therapeutically active substance(s), for example, an immune system modulator such as an interferon, interleukin, tumor necrosis factor or colony stimulating factor; an antiviral agent or an anti-inflammatory agent. When the treatment is combination therapy, such administration may be concurrent or sequential with respect to that of the 2'-deoxy-2'-fluoro nucleoside derivatives of the present invention. Concurrent administration, as used herein thus includes administration of the agents at the same time or at different times.

Administration of the active compound (2'-deoxy-2'-fluoro nucleoside derivatives) provided by the present invention, as well as their pharmaceutically useable salts, can be used as medicaments in the form of any pharmaceutical formulation, e.g. oral, topical, parenteral (or intrasternal injection or infusion techniques), e.g. in the form of injection solutions, nasally, e.g. in the form of nasal sprays, or inhalation spray, topically and so forth, intramuscular, intravenous, subcutaneous, transdermal (which may include a penetration enhancement agent), buccal and suppository administration and may range from a continuous intravenous drip to several oral administrations per day (for example, Q.I.D). Further, the pharmaceutical formulation can be administered enterally, either orally, e.g. in the form of tablets, coated tablets, dragées, hard and soft gelatine capsules, solutions, emulsions, syrups, or suspensions, or rectally, e.g. in the form of suppositories.

For the manufacture of pharmaceutical preparations, the 2'-deoxy-2'-fluoro nucleoside derivatives, as well as their pharmaceutically acceptable salts, can be formulated with a therapeutically inert, inorganic or organic excipient for the production of tablets, coated tablets, dragées, hard and soft gelatine capsules, solutions, emulsions or suspensions.

By way of example, it is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suitable excipients for tablets, coated tablets, dragées, and hard gelatin capsules are, for example, lactose, corn starch and derivatives thereof, talc, and stearic acid or its salts.

If desired, the tablets or capsules may be enteric-coated or sustained release by standard techniques.

Suitable excipients for soft gelatine capsules are, for example, vegetable oils, waxes, fats, semi-solid and liquid polyols.

Suitable excipients for injection solutions are, for example, water, saline, alcohols, polyols, glycerine or vegetable oils.

Suitable excipients for suppositories are, for example, natural and hardened oils, waxes, fats, semi-liquid or liquid polyols.

Suitable excipients for solutions and syrups for enteral use are, for example, water, polyols, saccharose, invert sugar and glucose.

The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants.

The pharmaceutical preparations may also contain other therapeutically active agents known in the art.

The 2'-deoxy-2'-fluoro nucleoside derivatives provided by the present invention are useful in the treatment of immune mediated conditions and diseases, viral diseases, bacterial diseases, parasitic diseases, inflammatory diseases, hyperproliferative vascular diseases, allograft rejection, tumours, and cancers.

The dosage can vary within wide limits and will, of course, be adjusted to the individual requirements in each particular case. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 100 mg/kg body weight per day. A typical preparation will contain from about 5% to about 95% active compound (w/w). The daily dosage can be administered as a single dosage or in divided dosages, typically between 1 and 5 dosages per day.

It will be understood that references herein to treatment extend to prophylaxis as well as to the treatment of existing conditions, and that the treatment of animals includes the treatment of humans as well as other mammals. Furthermore, the term "treatment of a hepatitis C virus (HCV) infection", as used herein, includes the treatment or prophylaxis of a disease or a condition associated with or mediated by hepatitis C virus (HCV) infection, or the clinical symptoms thereof.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The compounds of the present invention are known in the art and can be prepared by known methods, especially as described below:

EXAMPLE 1

2'-Deoxy-2'-fluorocytidine can be purchased from Sigma-Aldrich Company Ltd., Cat. No. F8883 or prepared by methods known to the art for example from 2,2'-O-anhydrocytidine as described by R Mengel and W Guschlbauer Angew Chemie Intl Ed 1978, 17, 525.

EXAMPLE 2

9-(2-Deoxy-2-fluoro-β-D-ribofuranosyl)-2,6-diaminopurine can be prepared by the method of H. J. Thomas et al, Nucleosides and Nucleotides, 1994, 13, 309.

EXAMPLE 3

2'-Deoxy-2'-fluoroguanosine can be prepared by the method of B. S. Ross et al, Nucleosides and Nucleotides, 1997, 16, 1645.

EXAMPLE 4

The 5'-O-triphosphate derivative of 2'-deoxy-2'-fluorocytidine can be purchased from Trilink BioTechnologies Inc., Cat. No. N-1008-1 or prepared by methods known to the art for example as described by K Burgess and D Cook Chemical Reviews 2000, 100, 2047.

Methods for the monophosphorylation of organic compounds including nucleosides have been reviewed by L A Slotin, Synthesis, 1977, 737. More recently other nucleoside phosphorylation procedures have been described: M Uchiyama et al J. Org. Chem., 1993, 58,373; R Caputo et al, Synlett., 1997, 739 and M Taktakishvili and V Nair Tet. Lett. 2000, 41, 7173. Other procedures for monophosphorylation that may be useful for nucleosides are described by C E McKenna and J Schmidhauser, J. Chem. Soc., Chem. Commun., 1979, 739 and J K Stowell and T S Widlanski Tet. Lett., 1995, 1825. Synthesis of di and triphosphate derivatives are reviewed in K H Scheit, Nucleotide Analogues, 1980, Wiley Interscience and by K Burgess and D Cook Chemical Reviews, 2000, 100, 2047.

The compounds represented by formula I may be prepared by any of the methods known in the art for the preparation of similar 2'-fluoronucleoside derivatives. E.g see P Herdewijn et al Nucleosides and Nucleotides, 1989, 8, 65 or H Hayakawa et al Chem Pharm Bull, 1990, 38, 1136 and in particular R Mengel and W Guschlbauer Angew Chemie Intl Ed 1978, 17, 525 or H J Thomas et al, Nucleosides and Nucleotides 1994, 13, 309 or B S Ross, et al, Nucleosides and Nucleotides, 1997, 16, 1645.

Such methods may be adapted for the synthesis of the alternative stereoisomers represented by formula I for example L-nucleosides. The general synthesis of L-nucleosides has been described (P Wang et al, Antiviral Research, 1998, 40, 19; E Moyroud and P Strazewski Tetrahedron, 1999, 55, 1277). Introduction of a 2'-fluoro substituent can be accomplished using the methods described for the corresponding D-nucleoside analogues in the references above.

Where synthesis of the compound of formula I employs a condensation reaction of a purine or pyrimidine base with a suitably protected 2-fluoro-furanose derivative such as that described by H J Thomas et al Nucleosides and Nucleotides, 1994, 13, 309, then mixtures of anomeric nucleoside derivatives will often result. The α and β-nucleosides can be separated by standard techniques known to the art such as recrystallisation, column chromatography, high performance liquid chromatography or super critical fluid chromatography.

Further information for the preparation of compounds of formula I or I-a can be deduced from the following references: WO 99/43691, WO 98/16184, C. R. Wagner et al Medicinal Research Reviews, 2000, 20(6), 417 or R. Jones and N. Bischofberger, Antiviral Research 1995, 27, 1).

What is claimed is:

1. A method for the treatment of hepatitis C virus (HCV) infection comprising administering a therapeutically effective amount of a compound of formula I-a

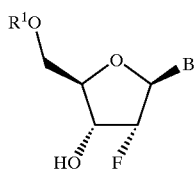

I-a wherein

R$^1$ is hydrogen or phosphate and

B is a 1-pyrimidinyl or 9-purinyl residue of formulae B1, B2 or B3

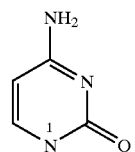

B1

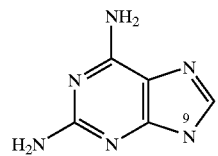

B2

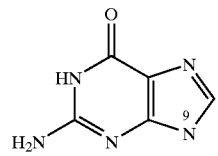

B3 and pharmaceutically acceptable salts thereof.

2. The method of claim 1 wherein

B is 1-pyrimidinyl, and pharmaceutically acceptable salts thereof.

3. The method of claim 1 wherein the compound is

2'-deoxy-2'-fluorocytidine, 9-(2-deoxy-2-fluoro-β-D-ribofuranosyl)-2,6-diaminopurine, 2'-deoxy-2'-fluoroguanosine, or 2'-deoxy-2'-fluorocytidine 5'-O-triphosphate mono lithium salt.

* * * * *